US006558933B2

(12) United States Patent
Donald et al.

(10) Patent No.: US 6,558,933 B2
(45) Date of Patent: May 6, 2003

(54) MUTANT 1,3-PROPANEDIOL DEHYDROGENASE

(75) Inventors: Trimbur E. Donald, Redwood City, CA (US); Whited M. Gregory, Belmont, CA (US); Olga V. Selifonova, Navarre, MN (US)

(73) Assignee: Genencor International, INC, Rochester, NY (US)

(*) Notice: Subject to any disclaimer, the term of this patent is extended or adjusted under 35 U.S.C. 154(b) by 0 days.

(21) Appl. No.: 09/991,138

(22) Filed: Nov. 16, 2001

(65) Prior Publication Data

US 2003/0040091 A1 Feb. 27, 2003

Related U.S. Application Data

(62) Division of application No. 09/570,778, filed on May 14, 2000.

(60) Provisional application No. 60/134,868, filed on May 19, 1999.

(51) Int. Cl.[7] ............................ C12N 9/09; C12N 1/20; C12N 15/00; C12P 7/18; C07H 21/04

(52) U.S. Cl. ........................ 435/190; 435/158; 435/157; 435/252.3; 435/320.1; 435/440; 576/23.2

(58) Field of Search ................................ 435/190, 440, 435/252.3, 320.1, 157, 158; 536/23.2

(56) References Cited

PUBLICATIONS

*Boronat et al., "Experimental Evolution of Propanediol Oxidoreductase in *Escherichia coli*, " *Biochimica et Biophysica Acta*, 672 (1981) p. 98–107.

*Daniel et al., "Purification of 1,3–Propanediol Dehydrogenase from *Citrabacter freundii* and Cloning, Sequencing, and Overexpression of the Corresponding Gene in *Escherichia coli*, " *Journal of Bacteriology*, Apr. 1995, p. 2151–2156.

*Obradors et al., "Site–directed mutagenesis studies of the metal–binding center of the iron–dependent propanediol oxidoreductase from *Escherichia coli*, " *Eur. J. Biochem*, 258, 207–213 (1998).

*Reimann et al., "1,3–Propanediol formation with product-Tolerant mutants of *Clostridium butyricum* DSM 5431 in continuous culture: productivity, carbon and electron flow," *Journal of Applied Microbiology 1998*, 84, p. 1125–1130.

*Primary Examiner*—Ponnathapu Achutamurthy
*Assistant Examiner*—Yong Pak
(74) *Attorney, Agent, or Firm*—Richard T. Ito

(57) ABSTRACT

The present invention relates to mutant 1,3-propanediol dehydrogenase and a novel microorganism that is capable of growing in concentrations of at least 105 g/l 1,3-propanediol, levels normally toxic to wild-type microorganisms. The present invention also provides expression vectors and host cells comprising the mutant 1,3-propanediol dehydrogenase as well as methods for producing 1,3-propanediol comprising the use of cells comprising the mutant 1,3-propanediol dehydrogenase.

22 Claims, 7 Drawing Sheets

Decoration 'Decoration #1': Outline residues that differ from the Consensus.

```
    10        20        30        40        50        60        70
10  ATGAGCTATCGTATGTTTGATTATCTGGTTCCAAATGTGAACTTCTTTGGCCCGGGCGCCGTTTCTGTTG  Eb_429T.dna
10  ATGAGCTATCGTATGTTTGATTATCTGGTTCCAAATGTRAACTTCTTTGGCCCGGGCGCCGTTTCTGTTG  Eb_GEBT.dna

    80        90        100       110       120       130       140
80  TTGGCCAGCGCTGCCAGCTGCTGGGGGGTAAAAAAGCCCTGCTGGTGACCGATAAGGGCCTGCGCGCCAT  Eb_429T.dna
80  TTGGCCAGCGCTGCCAGCTGCTGGGGGGTAAAAAAGCCCTGCTGGTGACCGATAAGGGCCTGCGCGCCAT  Eb_GEBT.dna

    150       160       170       180       190       200       210
150 TAAAGACGGTGCTGTCGATCAGACCGTGAAGCACCTGAAAGCCGCCGGTATTGAGGTGGTCATTTTCGAC  Eb_429T.dna
150 TAAAGACGGTGCTGTCGATCAGACCGTGAAGCACCTGAAAGCCGCCGGTATTGAGGTGGTCATTTTCGAC  Eb_GEBT.dna

    220       230       240       250       260       270       280
220 GGGGTCGAGCCGAACCCGAAAGACACCAACGTGCTCGACGGCCTGGCCATGTTCCGTAAAGAGCAGTGCG  Eb_429T.dna
220 GGGGTCGAGCCGAACCCGAAAGACACCAACGTGCTCGACGGCCTGGCCATGTTCCGTAAAGAGCAGTGCG  Eb_GEBT.dna

    290       300       310       320       330       340       350
290 ACATGATAATCACCGTCGGCGGCGGCAGCCCGCACGACTGCGGTAAAGGCATTGGTATTGCGGCCACCCA  Eb_429T.dna
290 ACATGATAATCACCGTCGGCGGCGGCAGCCCGCTCGACTGCGGTAAAGGCATTGGTATTGCGGCCACCCA  Eb_GEBT.dna

    360       370       380       390       400       410       420
360 CCCGGGTGATCTGTACAGCTATGCCGGTATCGAAACACTCACCAACCCGCTGCCGCCCATTATTGCGGTC  Eb_429T.dna
360 CCCGGGTGATCTGTACAGCTATGCCGGTATCGAAACACTCACCAACCCGCTGCCGCCCATTATTGCGGTC  Eb_GEBT.dna
```

FIG._1A

```
430 AACACCACCGCCGGGACCGCCAGCGAAGTCACCCGCCACTGCGTGCTGACTAACACCAAAACCAAAGTAA Eb_429T.dna
430 AACACCACCGCCGGGACCGCCAGCGAAGTCACCCGCCACTGCGTGCTGACTAACACCAAAACCAAAGTAA Eb_GEBT.dna

500 AATTTGTGATTGTCAGCTGGCGCAACCTGCCTTCCGTCTCCATTAACGATCCGCTGCTGATGATCGGCAA Eb_429T.dna
500 AATTTGTGATTGTCAGCTGGCGCAACCTGCCTTCCGTCTCCATTAACGATCCGCTGCTGATGATCGGCAA Eb_GEBT.dna

570 GCCCGCCGGGCTGACCGCCGCCACCGGTATGGATGCCCTGACCCACGCGGTAGAGGCCTATATCTCCAAA Eb_429T.dna
570 GCCCGCCGGGCTGACCGCCGCCACCGGTATGGATGCCCTGACCCACGCGGTAGAGGCCTATATCTCCAAA Eb_GEBT.dna

640 GACGCCAACCCGGTTACCGATGCCTCTGCTATTCAGGCCATCAAACTGATTGCCACCAACTTGCGCCAGG Eb_429T.dna
640 GACGCCAACCCGGTTACCGATGCCTCTGCTATTCAGGCCATCAAACTGATTGCCACCAACTTGCGCCAGG Eb_GEBT.dna

710 CCGTCGCCCTGGGGACCAACCTCAAAGCCCGTGAAAACATGGCCTGCGCCTCTCTGCTGGCCGGGATGGC Eb_429T.dna
710 CCGTCGCCCTGGGGACCAACCTCAAAGCCCGTGAAAACATGGCCTGCGCCTCTCTGCTGGCCGGGATGGC Eb_GEBT.dna

780 CTTTAACAACGCCAACCTGGGCTATGTTCACGCCATGGCTCACCAGCTGGGCGGCCTGTACGACATGGCC Eb_429T.dna
780 CTTTAACAACGCCAACCTGGGCTATGTTCACGCCATGGCTCACCAGCTGGGCGGCCTGTACGACATGGCC Eb_GEBT.dna
```

FIG._1B

```
850  CACGGGGTGGCGAACGCGGTCCTGCTGCCCCATGTCTGCCGCTATAACCTGATTGCCAACCCGGAAAAAT  Eb_429T.dna
850  CACGGGGTGGCGAACGCGGTCCTGCTGCCCCATGTCTGCCGCTATAACCTGATTGCCAACCCGGAAAAAT  Eb_GEBT.dna

920  TTGCCGATATCGCCACCTTTATGGGGGAAAACACCACCGGTCTTTCCACCATGGACGCAGCGGAGCTGGC  Eb_429T.dna
920  TTGCCGATATCGCCACCTTTATGGGGGAAAACACCACCGGTCTTTCCACCATGGACGCAGCGGAGCTGGC  Eb_GEBT.dna

990  CATCAGCGCCATTGCCCGTCTGTCTAAAGATGTCGGGATCCCGCAGCACCTGCGTGAACTGGGGGTAAAA  Eb_429T.dna
990  CATCAGCGCCATTGCCCGTCTGTCTAAAGATGTCGGGATCCCGCAGCACCTGCGTGAACTGGGGGTAAAA  Eb_GEBT.dna

1060 GAGGCCGACTTCCCGTACATGGCAGAAATGGCCCTGAAAGACGGCAACGCCTTCTCTAACCCGCGCAAAG  Eb_429T.dna
1060 GAGGCCGACTTCCCGTACATGGCAGAAATGGCCCTGAAAGACGGCAACGCCTTCTCTAACCCGCGCAAAG  Eb_GEBT.dna

1130 GGAACGAAAAAGAGATTGCCGACATTTTCCGCCAGGCATTCTGA  Eb_429T.dna
1130 GGAACGAAAAAGAGATTGCCGACATTTTCCGCCAGGCATTCTGA  Eb_GEBT.dna
```

Decoration 'Decoration #1': Outline residues that differ from the Consensus.

FIG._1C

```
     10        40        70        100       130       160
10   MSYRMFDYLVPNVNFFGPGAVSVVGQRCQLLGGKKALLVTDKGLRAIKDGAVDQTVKHLK Eb_429T.dna
10   MSYRMFDYLVPNVNFFGPGAVSVVGQRCQLLGGKKALLVTDKGLRAIKDGAVDQTVKHLK Eb_GEBT.dna

     190       220       250       280       310       340
190  AAGIEVVIFDGVEPNPKDTNVLDGLAMFRKEQCDMIITVGGGSPHDCGKGIGIAATHPGD Eb_429T.dna
190  AAGIEVVIFDGVEPNPKDTNVLDGLAMFRKEQCDMIITVGGGSPLDCGKGIGIAATHPGD Eb_GEBT.dna

     370       400       430       460       490       520
370  LYSYAGIETLTNPLPPIIAVNTTAGTASEVTRHCVLTNTKTKVKFVIVSWRNLPSVSIND Eb_429T.dna
370  LYSYAGIETLTNPLPPIIAVNTTAGTASEVTRHCVLTNTKTKVKFVIVSWRNLPSVSIND Eb_GEBT.dna

     550       580       610       640       670       700
550  PLLMIGKPAGLTAATGMDALTHAVEAYISKDANPVTDASAIQAIKLIATNLRQAVALGTN Eb_429T.dna
550  PLLMIGKPAGLTAATGMDALTHAVEAYISKDANPVTDASAIQAIKLIATNLRQAVALGTN Eb_GEBT.dna

     730       760       790       820       850       880
730  LKARENMACASLLAGMAFNNANLGYVHAMAHQLGGLYDMAHGVANAVLLPHVCRYNLIAN Eb_429T.dna
730  LKARENMACASLLAGMAFNNANLGYVHAMAHQLGGLYDMAHGVANAVLLPHVCRYNLIAN Eb_GEBT.dna

     910       940       970       1000      1030      1060
910  PEKFADIATFMGENTTGLSTMDAAELAISAIARLSKDVGIPQHLRELGVKEADFPYMAEM Eb_429T.dna
910  PEKFADIATFMGENTTGLSTMDAAELAISAIARLSKDVGIPQHLRELGVKEADFPYMAEM Eb_GEBT.dna

     1090      1120      1150
1090 ALKDGNAFSNPRKGNEKEIADIFRQAF.                                 Eb_429T.dna
1090 ALKDGNAFSNPRKGNEKEIADIFRQAF.                                 Eb_GEBT.dna
```

Decoration 'Decoration #1': Outline residues that differ from the Consensus.

FIG._2

```
    MSYRMFDYLVPNVNFFGPGAVSVVGERCQLLGGKKALLVTDKGLRAIKDGAVDQTVKHLK Majority
             10        20        30        40        50        60
  1 MSYRMFDYLVPNVNFFGPGAVSVVGQRCQLLGGKKALLVTDKGLRAIKDGAVDQTVKHLK Eb_GEBT.aa
  1 MSYRMFDYLVPNVNFFGPGAVSVVGQRCQLLGGKKALLVTDKGLRAIKDGAVDQTVKHLK Eb_429T.aa
  1 MSYRMFDYLVPNVNFFGPGAVSVVGQRCQLLGGKKALLVTDKGLRAIKDGAVDQTVKHLK Eb_907T.aa
  1 MSYRMFDYLVPNVNFFGPNAISVVGERCQLLGGKKALLVTDKGLRAIKDGAVDKTLHYLR Kpn_dhaT.dna
  1 MSYRMFDYLVPNVNFFGPNAISVVGERCKLLGGKKALLVTDKGLRAIKDGAVDKTLTHLR Cfu_dhaT.dna
  1 --MRMYDFLAPNVNFMGAGAIKLVGERCKILGGKKALIVTDKFLRNMEDGAVAQTVKYIK Cpast_dhaT.dna

    AAGIEVVIFDGVEPNPKDTNVLDGLAVFRKEQCDMIVTVGGGSPHDCGKGIGIAATHEGD Majority
             70        80        90       100       110       120
 61 AAGIEVVIFDGVEPNPKDTNVLDGLAMFRKEQCDMIITVGGGSPLDCGKGIGIAATHPGD Eb_GEBT.aa
 61 AAGIEVVIFDGVEPNPKDTNVLDGLAMFRKEQCDMIITVGGGSPHDCGKGIGIAATHPGD Eb_429T.aa
 61 AAGIEVVIFDGVEPNPKDTNVLDGLAMFRKEQCDMIITVGGGSPHDCGKGIGIAATHPGD Eb_907T.aa
181 EAGIEVAIFDGVEPNPKDTNVRDGLAVFRREQCDIIVTVGGGSPHDCGKGIGIAATHEGD Kpn_dhaT.dna
181 EAGIDVVVFDGVEPNPKDTNVRDGLEVFRKEHCDIIVTVGGGSPHDCGKGIGIAATHEGD Cfu_dhaT.dna
175 EAGIDVAFYDDVEPNPKDTNVRDGLKVYRKENCDLIVTVGGGSSHDCGKGIGIAATHEGD Cpast_dhaT.dna

    LYSYAGIETLTNPLPPIVAVNTTAGTASEVTRHCVLTNTKTKVKFVIVSWRNLPSVSIND Majority
            130       140       150       160       170       180
121 LYSYAGIETLTNPLPPIIAVNTTAGTASEVTRHCVLTNTKTKVKFVIVSWRNLPSVSIND Eb_GEBT.aa
121 LYSYAGIETLTNPLPPIIAVNTTAGTASEVTRHCVLTNTKTKVKFVIVSWRNLPSVSIND Eb_429T.aa
121 LYSYAGIETLTNPLPPIIAVNTTAGTASEVTRHCVLTNTKTKVKFVIVSWRNLPSVSIND Eb_907T.aa
361 LYQYAGIETLTNPLPPIVAVNTTAGTASEVTRHCVLTNTETKVKFVIVSWRNLPSVSIND Kpn_dhaT.dna
361 LYSYAGIETLTNPLPPIVAVNTTAGTASEVTRHCVLTNTKTKVKFVIVSWRNLPSVSIND Cfu_dhaT.dna
355 LYDYAGIETLTNPLPPIVAVNTTAGTGSEVTRHCVITNTKTKIKFVIVSWRNLPLVSIND Cpast_dhaT.dna
```

FIG._3A

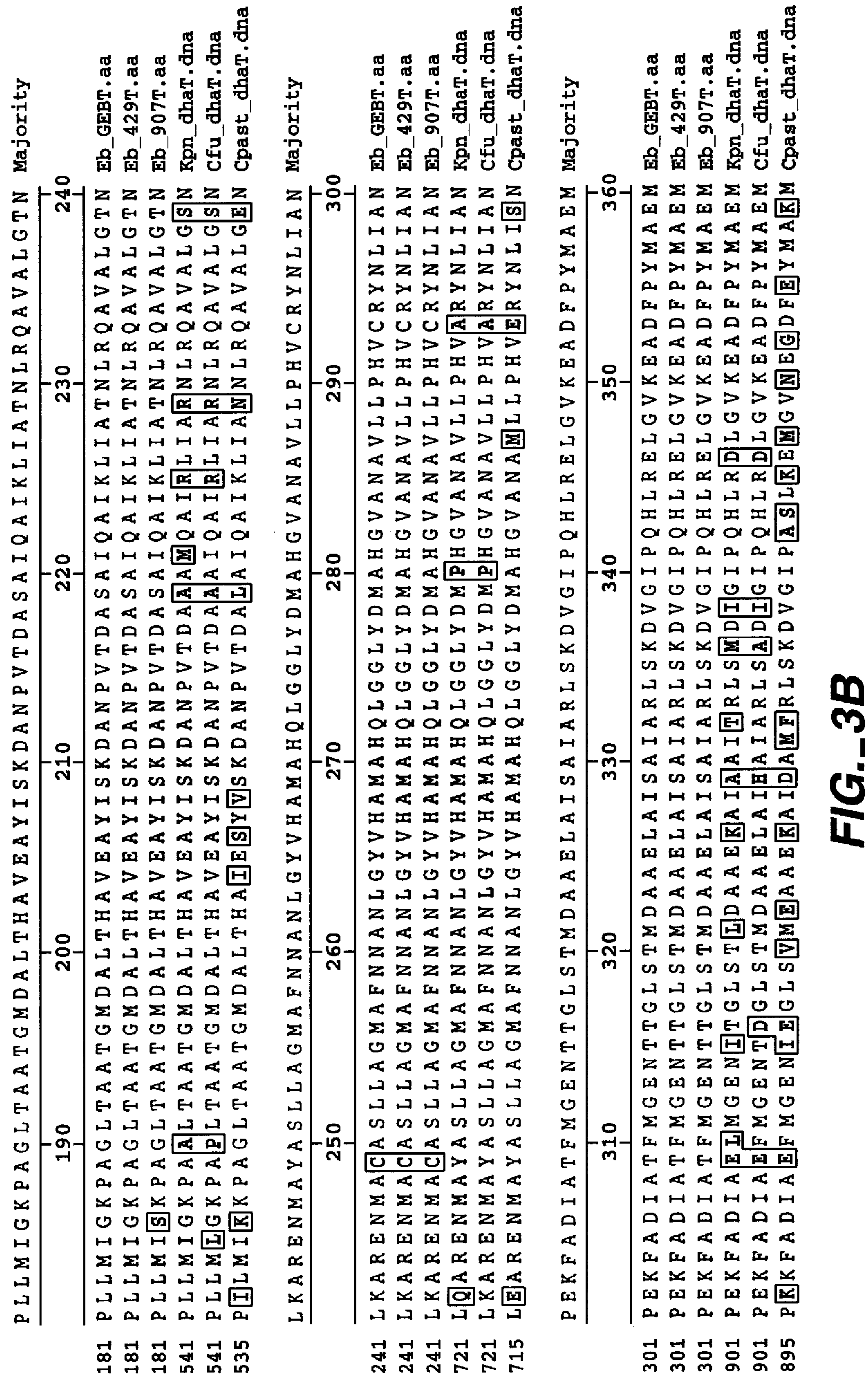
FIG._3B

```
       ALKDGNAFSNPRKGNEKEIADIFRQAF-    Majority
                 370       380
 361   ALKDGNAFSNPRKGNEKEIADIFRQAF.    Eb_GEBT.aa
 361   ALKDGNAFSNPRKGNEKEIADIFRQAF.    Eb_429T.aa
 361   ALKDGNAFSNPRKGNEKEIADIFRQAF.    Eb_907T.aa
1081   ALKDGNAFSNPRKGNEQEIAAIFRQAF.    Kpn_dhaT.dna
1081   ALKDGNAFSNPRKGNEKEIAEIFRQAF.    Cfu_dhaT.dna
1075   ALKDGNAFSNPRKGNEKDIVKIFREAF.    Cpast_dhaT.dna
```

Decoration 'Decoration #1': Outline residues that differ from the Consensus.

FIG._3C

SEQUENCE LISTING

<160> NUMBER OF SEQ ID NOS: 12

<210> SEQ ID NO 1
<211> LENGTH: 1164
<212> TYPE: DNA
<213> ORGANISM: Escherichia blattae

<400> SEQUENCE: 1

```
atgagctatc gtatgtttga ttatctggtt ccaaatgtra acttctttgg cccgggcgcc     60

gtttctgttg ttggccagcg ctgccagctg ctgggggggta aaaaagccct gctggtgacc   120

gataagggcc tgcgcgccat taaagacggt gctgtcgatc agaccgtgaa gcacctgaaa   180

gccgccggta ttgaggtggt cattttcgac ggggtcgagc cgaacccgaa agacaccaac   240

gtgctcgacg gcctggccat gttccgtaaa gagcagtgcg acatgataat caccgtcggc   300

ggcggcagcc cgctcgactg cggtaaaggc attggtattg cggccaccca cccgggtgat   360

ctgtacagct atgccggtat cgaaacactc accaacccgc tgccgcccat tattgcggtc   420

aacaccaccg ccgggaccgc cagcgaagtc acccgccact gcgtgctgac taacaccaaa   480

accaaagtaa aatttgtgat tgtcagctgg cgcaacctgc cttccgtctc cattaacgat   540

ccgctgctga tgatcggcaa gcccgccggg ctgaccgccg ccaccggtat ggatgccctg   600

acccacgcgg tagaggccta tatctccaaa gacgccaacc cggttaccga tgcctctgct   660

attcaggcca tcaaactgat tgccaccaac ttgcgccagg ccgtcgccct ggggaccaac   720

ctcaaagccc gtgaaaacat ggcctgcgcc tctctgctgg ccgggatggc ctttaacaac   780

gccaacctgg gctatgttca cgccatggct caccagctgg gcggcctgta cgacatggcc   840

cacggggtgg cgaacgcggt cctgctgccc catgtctgcc gctataacct gattgccaac   900

ccggaaaaat ttgccgatat cgccaccttt atgggggaaa acaccaccgg tctttccacc   960

atggacgcag cggagctggc catcagcgcc attgcccgtc tgtctaaaga tgtcgggatc  1020

ccgcagcacc tgcgtgaact gggggtaaaa gaggccgact tcccgtacat ggcagaaatg  1080

gccctgaaag acggcaacgc cttctctaac ccgcgcaaag ggaacgaaaa agagattgcc  1140

gacattttcc gccaggcatt ctga                                          1164
```

<210> SEQ ID NO 2
<211> LENGTH: 387
<212> TYPE: PRT
<213> ORGANISM: Escherichia blattae

<400> SEQUENCE: 2

```
Met Ser Tyr Arg Met Phe Asp Tyr Leu Val Pro Asn Val Asn Phe Phe
 1               5                  10                  15

Gly Pro Gly Ala Val Ser Val Val Gly Gln Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Gln Thr Val Lys His Leu Lys Ala Ala Gly Ile
    50                  55                  60

Glu Val Val Ile Phe Asp Gly Val Glu Pro Asn Pro Lys Asp Thr Asn
65                  70                  75                  80

Val Leu Asp Gly Leu Ala Met Phe Arg Lys Glu Gln Cys Asp Met Ile
                85                  90                  95

Ile Thr Val Gly Gly Gly Ser Pro Leu Asp Cys Gly Lys Gly Ile Gly
```

-continued

```
            100                 105                 110

Ile Ala Ala Thr His Pro Gly Asp Leu Tyr Ser Tyr Ala Gly Ile Glu
        115                 120                 125

Thr Leu Thr Asn Pro Leu Pro Pro Ile Ile Ala Val Asn Thr Thr Ala
    130                 135                 140

Gly Thr Ala Ser Glu Val Thr Arg His Cys Val Leu Thr Asn Thr Lys
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Gly Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ser Ala Ile Gln Ala Ile
    210                 215                 220

Lys Leu Ile Ala Thr Asn Leu Arg Gln Ala Val Ala Leu Gly Thr Asn
225                 230                 235                 240

Leu Lys Ala Arg Glu Asn Met Ala Cys Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Ala His Gly Val Ala Asn Ala Val Leu
        275                 280                 285

Leu Pro His Val Cys Arg Tyr Asn Leu Ile Ala Asn Pro Glu Lys Phe
    290                 295                 300

Ala Asp Ile Ala Thr Phe Met Gly Glu Asn Thr Thr Gly Leu Ser Thr
305                 310                 315                 320

Met Asp Ala Ala Glu Leu Ala Ile Ser Ala Ile Ala Arg Leu Ser Lys
                325                 330                 335

Asp Val Gly Ile Pro Gln His Leu Arg Glu Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Lys Glu Ile Ala Asp Ile Phe Arg
    370                 375                 380

Gln Ala Phe
385


<210> SEQ ID NO 3
<211> LENGTH: 36
<212> TYPE: DNA
<213> ORGANISM: Artificial Sequence
<220> FEATURE:
<223> OTHER INFORMATION: primer

<400> SEQUENCE: 3

tctgatacgg gatcctcaga atgcctggcg gaaaat                              36


<210> SEQ ID NO 4
<211> LENGTH: 42
<212> TYPE: DNA
<213> ORGANISM: Artificial Sequence
<220> FEATURE:
<223> OTHER INFORMATION: primer

<400> SEQUENCE: 4

gcgccgtcta gaattatgag ctatcgtatg tttgattatc tg                       42
```

-continued

<210> SEQ ID NO 5
<211> LENGTH: 1164
<212> TYPE: DNA
<213> ORGANISM: Escherichia blattae

<400> SEQUENCE: 5
atgagctatc gtatgtttga ttatctggtt ccaaatgtga acttctttgg cccgggcgcc 60
gtttctgttg ttggccagcg ctgccagctg ctggggggta aaaaagccct gctggtgacc 120
gataagggcc tgcgcgccat taaagacggt gctgtcgatc agaccgtgaa gcacctgaaa 180
gccgccggta ttgaggtggt cattttcgac ggggtcgagc cgaacccgaa agacaccaac 240
gtgctcgacg gcctggccat gttccgtaaa gagcagtgcg acatgataat caccgtcggc 300
ggcggcagcc cgcacgactg cggtaaaggc attggtattg cggccaccca cccgggtgat 360
ctgtacagct atgccggtat cgaaacactc accaacccgc tgccgcccat tattgcggtc 420
aacaccaccg ccgggaccgc cagcgaagtc acccgccact gcgtgctgac taacaccaaa 480
accaaagtaa aatttgtgat tgtcagctgg cgcaacctgc cttccgtctc cattaacgat 540
ccgctgctga tgatcggcaa gcccgccggg ctgaccgccg ccaccggtat ggatgccctg 600
acccacgcgg tagaggccta tatctccaaa gacgccaacc cggttaccga tgcctctgct 660
attcaggcca tcaaactgat tgccaccaac ttgcgccagg ccgtcgccct ggggaccaac 720
ctcaaagccc gtgaaaacat ggcctgcgcc tctctgctgg ccgggatggc ctttaacaac 780
gccaacctgg gctatgttca cgccatggct caccagctgg gcggcctgta cgacatggcc 840
cacggggtgg cgaacgcggt cctgctgccc catgtctgcc gctataacct gattgccaac 900
ccggaaaaat ttgccgatat cgccaccttt atgggggaaa acaccaccgg tctttccacc 960
atggacgcag cggagctggc catcagcgcc attgcccgtc tgtctaaaga tgtcgggatc 1020
ccgcagcacc tgcgtgaact gggggtaaaa gaggccgact tcccgtacat ggcagaaatg 1080
gccctgaaag acggcaacgc cttctctaac ccgcgcaaag ggaacgaaaa agagattgcc 1140
gacattttcc gccaggcatt ctga 1164

<210> SEQ ID NO 6
<211> LENGTH: 1164
<212> TYPE: DNA
<213> ORGANISM: Escherichia blattae

<400> SEQUENCE: 6
atgagctatc gtatgtttga ttatctggtt ccaaatgtra acttctttgg cccgggcgcc 60
gtttctgttg ttggccagcg ctgccagctg ctggggggta aaaaagccct gctggtgacc 120
gataagggcc tgcgcgccat taaagacggt gctgtcgatc agaccgtgaa gcacctgaaa 180
gccgccggta ttgaggtggt cattttcgac ggggtcgagc cgaacccgaa agacaccaac 240
gtgctcgacg gcctggccat gttccgtaaa gagcagtgcg acatgataat caccgtcggc 300
ggcggcagcc cgctcgactg cggtaaaggc attggtattg cggccaccca cccgggtgat 360
ctgtacagct atgccggtat cgaaacactc accaacccgc tgccgcccat tattgcggtc 420
aacaccaccg ccgggaccgc cagcgaagtc acccgccact gcgtgctgac taacaccaaa 480
accaaagtaa aatttgtgat tgtcagctgg cgcaacctgc cttccgtctc cattaacgat 540
ccgctgctga tgatcggcaa gcccgccggg ctgaccgccg ccaccggtat ggatgccctg 600
acccacgcgg tagaggccta tatctccaaa gacgccaacc cggttaccga tgcctctgct 660

-continued

```
attcaggcca tcaaactgat tgccaccaac ttgcgccagg ccgtcgccct ggggaccaac    720

ctcaaagccc gtgaaaacat ggcctgcgcc tctctgctgg ccgggatggc ctttaacaac    780

gccaacctgg gctatgttca cgccatggct caccagctgg gcggcctgta cgacatggcc    840

cacggggtgg cgaacgcggt cctgctgccc catgtctgcc gctataacct gattgccaac    900

ccggaaaaat ttgccgatat cgccaccttt atgggggaaa acaccaccgg tctttccacc    960

atggacgcag cggagctggc catcagcgcc attgcccgtc tgtctaaaga tgtcgggatc   1020

ccgcagcacc tgcgtgaact gggggtaaaa gaggccgact tcccgtacat ggcagaaatg   1080

gccctgaaag acggcaacgc cttctctaac ccgcgcaaag ggaacgaaaa agagattgcc   1140

gacattttcc gccaggcatt ctga                                          1164


<210> SEQ ID NO 7
<211> LENGTH: 387
<212> TYPE: PRT
<213> ORGANISM: Escherichia blattae

<400> SEQUENCE: 7

Met Ser Tyr Arg Met Phe Asp Tyr Leu Val Pro Asn Val Asn Phe Phe
 1               5                  10                  15

Gly Pro Gly Ala Val Ser Val Val Gly Gln Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Gln Thr Val Lys His Leu Lys Ala Ala Gly Ile
    50                  55                  60

Glu Val Val Ile Phe Asp Gly Val Glu Pro Asn Pro Lys Asp Thr Asn
65                  70                  75                  80

Val Leu Asp Gly Leu Ala Met Phe Arg Lys Glu Gln Cys Asp Met Ile
                85                  90                  95

Ile Thr Val Gly Gly Gly Ser Pro His Asp Cys Gly Lys Gly Ile Gly
            100                 105                 110

Ile Ala Ala Thr His Pro Gly Asp Leu Tyr Ser Tyr Ala Gly Ile Glu
        115                 120                 125

Thr Leu Thr Asn Pro Leu Pro Pro Ile Ile Ala Val Asn Thr Thr Ala
    130                 135                 140

Gly Thr Ala Ser Glu Val Thr Arg His Cys Val Leu Thr Asn Thr Lys
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Gly Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ser Ala Ile Gln Ala Ile
    210                 215                 220

Lys Leu Ile Ala Thr Asn Leu Arg Gln Ala Val Ala Leu Gly Thr Asn
225                 230                 235                 240

Leu Lys Ala Arg Glu Asn Met Ala Cys Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Ala His Gly Val Ala Asn Ala Val Leu
        275                 280                 285
```

-continued

Leu Pro His Val Cys Arg Tyr Asn Leu Ile Ala Asn Pro Glu Lys Phe
290 295 300

Ala Asp Ile Ala Thr Phe Met Gly Glu Asn Thr Thr Gly Leu Ser Thr
305 310 315 320

Met Asp Ala Ala Glu Leu Ala Ile Ser Ala Ile Ala Arg Leu Ser Lys
325 330 335

Asp Val Gly Ile Pro Gln His Leu Arg Glu Leu Gly Val Lys Glu Ala
340 345 350

Asp Phe Pro Tyr Met Ala Glu Met Ala Leu Lys Asp Gly Asn Ala Phe
355 360 365

Ser Asn Pro Arg Lys Gly Asn Glu Lys Glu Ile Ala Asp Ile Phe Arg
370 375 380

Gln Ala Phe
385

<210> SEQ ID NO 8
<211> LENGTH: 387
<212> TYPE: PRT
<213> ORGANISM: Escherichia blattae

<400> SEQUENCE: 8

Met Ser Tyr Arg Met Phe Asp Tyr Leu Val Pro Asn Val Asn Phe Phe
1 5 10 15

Gly Pro Gly Ala Val Ser Val Val Gly Gln Arg Cys Gln Leu Leu Gly
20 25 30

Gly Lys Lys Ala Leu Leu Val Thr Asp Lys Gly Leu Arg Ala Ile Lys
35 40 45

Asp Gly Ala Val Asp Gln Thr Val Lys His Leu Lys Ala Ala Gly Ile
50 55 60

Glu Val Val Ile Phe Asp Gly Val Glu Pro Asn Pro Lys Asp Thr Asn
65 70 75 80

Val Leu Asp Gly Leu Ala Met Phe Arg Lys Glu Gln Cys Asp Met Ile
85 90 95

Ile Thr Val Gly Gly Gly Ser Pro Leu Asp Cys Gly Lys Gly Ile Gly
100 105 110

Ile Ala Ala Thr His Pro Gly Asp Leu Tyr Ser Tyr Ala Gly Ile Glu
115 120 125

Thr Leu Thr Asn Pro Leu Pro Pro Ile Ile Ala Val Asn Thr Thr Ala
130 135 140

Gly Thr Ala Ser Glu Val Thr Arg His Cys Val Leu Thr Asn Thr Lys
145 150 155 160

Thr Lys Val Lys Phe Val Ile Val Ser Trp Arg Asn Leu Pro Ser Val
165 170 175

Ser Ile Asn Asp Pro Leu Leu Met Ile Gly Lys Pro Ala Gly Leu Thr
180 185 190

Ala Ala Thr Gly Met Asp Ala Leu Thr His Ala Val Glu Ala Tyr Ile
195 200 205

Ser Lys Asp Ala Asn Pro Val Thr Asp Ala Ser Ala Ile Gln Ala Ile
210 215 220

Lys Leu Ile Ala Thr Asn Leu Arg Gln Ala Val Ala Leu Gly Thr Asn
225 230 235 240

Leu Lys Ala Arg Glu Asn Met Ala Cys Ala Ser Leu Leu Ala Gly Met
245 250 255

Ala Phe Asn Asn Ala Asn Leu Gly Tyr Val His Ala Met Ala His Gln

-continued

```
            260                 265                 270

Leu Gly Gly Leu Tyr Asp Met Ala His Gly Val Ala Asn Ala Val Leu
        275                 280                 285

Leu Pro His Val Cys Arg Tyr Asn Leu Ile Ala Asn Pro Glu Lys Phe
    290                 295                 300

Ala Asp Ile Ala Thr Phe Met Gly Glu Asn Thr Thr Gly Leu Ser Thr
305                 310                 315                 320

Met Asp Ala Ala Glu Leu Ala Ile Ser Ala Ile Ala Arg Leu Ser Lys
                325                 330                 335

Asp Val Gly Ile Pro Gln His Leu Arg Glu Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Lys Glu Ile Ala Asp Ile Phe Arg
    370                 375                 380

Gln Ala Phe
385


<210> SEQ ID NO 9
<211> LENGTH: 387
<212> TYPE: PRT
<213> ORGANISM: Escherichia blattae

<400> SEQUENCE: 9

Met Ser Tyr Arg Met Phe Asp Tyr Leu Val Pro Asn Val Asn Phe Phe
 1               5                  10                  15

Gly Pro Gly Ala Val Ser Val Val Gly Gln Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Gln Thr Val Lys His Leu Lys Ala Ala Gly Ile
    50                  55                  60

Glu Val Val Ile Phe Asp Gly Val Glu Pro Asn Pro Lys Asp Thr Asn
65                  70                  75                  80

Val Leu Asp Gly Leu Ala Met Phe Arg Lys Glu Gln Cys Asp Met Ile
                85                  90                  95

Ile Thr Val Gly Gly Gly Ser Pro His Asp Cys Gly Lys Gly Ile Gly
            100                 105                 110

Ile Ala Ala Thr His Pro Gly Asp Leu Tyr Ser Tyr Ala Gly Ile Glu
        115                 120                 125

Thr Leu Thr Asn Pro Leu Pro Pro Ile Ile Ala Val Asn Thr Thr Ala
    130                 135                 140

Gly Thr Ala Ser Glu Val Thr Arg His Cys Val Leu Thr Asn Thr Lys
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Ser Lys Pro Ala Gly Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ser Ala Ile Gln Ala Ile
    210                 215                 220

Lys Leu Ile Ala Thr Asn Leu Arg Gln Ala Val Ala Leu Gly Thr Asn
225                 230                 235                 240
```

-continued

```
Leu Lys Ala Arg Glu Asn Met Ala Cys Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Ala His Gly Val Ala Asn Ala Val Leu
        275                 280                 285

Leu Pro His Val Cys Arg Tyr Asn Leu Ile Ala Asn Pro Glu Lys Phe
    290                 295                 300

Ala Asp Ile Ala Thr Phe Met Gly Glu Asn Thr Thr Gly Leu Ser Thr
305                 310                 315                 320

Met Asp Ala Ala Glu Leu Ala Ile Ser Ala Ile Ala Arg Leu Ser Lys
                325                 330                 335

Asp Val Gly Ile Pro Gln His Leu Arg Glu Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Lys Glu Ile Ala Asp Ile Phe Arg
    370                 375                 380

Gln Ala Phe
385


<210> SEQ ID NO 10
<211> LENGTH: 387
<212> TYPE: PRT
<213> ORGANISM: Klebsiella pneumoniae

<400> SEQUENCE: 10

Met Ser Tyr Arg Met Phe Asp Tyr Leu Val Pro Asn Val Asn Phe Phe
 1               5                  10                  15

Gly Pro Asn Ala Ile Ser Val Val Gly Glu Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu His Tyr Leu Arg Glu Ala Gly Ile
    50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Gln Tyr Ala Gly Ile Glu
        115                 120                 125

Thr Leu Thr Asn Pro Leu Pro Pro Ile Val Ala Val Asn Thr Thr Ala
    130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Ala Met Gln Ala Ile
    210                 215                 220
```

-continued

```
Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ala Ile Thr Arg Leu Ser Met
                325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Gln Glu Ile Ala Ala Ile Phe Arg
    370                 375                 380

Gln Ala Phe
385
```

<210> SEQ ID NO 11
<211> LENGTH: 387
<212> TYPE: PRT
<213> ORGANISM: Citrobacter freundii

<400> SEQUENCE: 11

```
Met Ser Tyr Arg Met Phe Asp Tyr Leu Val Pro Asn Val Asn Phe Phe
 1               5                  10                  15

Gly Pro Asn Ala Ile Ser Val Val Gly Glu Arg Cys Lys Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu Thr His Leu Arg Glu Ala Gly Ile
    50                  55                  60

Asp Val Val Val Phe Asp Gly Val Glu Pro Asn Pro Lys Asp Thr Asn
65                  70                  75                  80

Val Arg Asp Gly Leu Glu Val Phe Arg Lys Glu His Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Ser Tyr Ala Gly Ile Glu
        115                 120                 125

Thr Leu Thr Asn Pro Leu Pro Pro Ile Val Ala Val Asn Thr Thr Ala
    130                 135                 140

Gly Thr Ala Ser Glu Val Thr Arg His Cys Val Leu Thr Asn Thr Lys
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Leu Gly Lys Pro Ala Pro Leu Thr
            180                 185                 190

Ala Ala Thr Gly Met Asp Ala Leu Thr His Ala Val Glu Ala Tyr Ile
```

-continued

```
        195                 200                 205

Ser Lys Asp Ala Asn Pro Val Thr Asp Ala Ala Ala Ile Gln Ala Ile
    210                 215                 220

Arg Leu Ile Ala Arg Asn Leu Arg Gln Ala Val Ala Leu Gly Ser Asn
225                 230                 235                 240

Leu Lys Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Phe Met Gly Glu Asn Thr Asp Gly Leu Ser Thr
305                 310                 315                 320

Met Asp Ala Ala Glu Leu Ala Ile His Ala Ile Ala Arg Leu Ser Ala
                325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Lys Glu Ile Ala Glu Ile Phe Arg
    370                 375                 380

Gln Ala Phe
385


<210> SEQ ID NO 12
<211> LENGTH: 385
<212> TYPE: PRT
<213> ORGANISM: Clostridium pasteurianum

<400> SEQUENCE: 12

Met Arg Met Tyr Asp Phe Leu Ala Pro Asn Val Asn Phe Met Gly Ala
 1               5                  10                  15

Gly Ala Ile Lys Leu Val Gly Glu Arg Cys Lys Ile Leu Gly Gly Lys
            20                  25                  30

Lys Ala Leu Ile Val Thr Asp Lys Phe Leu Arg Asn Met Glu Asp Gly
        35                  40                  45

Ala Val Ala Gln Thr Val Lys Tyr Ile Lys Glu Ala Gly Ile Asp Val
    50                  55                  60

Ala Phe Tyr Asp Asp Val Glu Pro Asn Pro Lys Asp Thr Asn Val Arg
65                  70                  75                  80

Asp Gly Leu Lys Val Tyr Arg Lys Glu Asn Cys Asp Leu Ile Val Thr
                85                  90                  95

Val Gly Gly Gly Ser Ser His Asp Cys Gly Lys Gly Ile Gly Ile Ala
            100                 105                 110

Ala Thr His Glu Gly Asp Leu Tyr Asp Tyr Ala Gly Ile Glu Thr Leu
        115                 120                 125

Thr Asn Pro Leu Pro Pro Ile Val Ala Val Asn Thr Thr Ala Gly Thr
    130                 135                 140

Gly Ser Glu Val Thr Arg His Cys Val Ile Thr Asn Thr Lys Thr Lys
145                 150                 155                 160

Ile Lys Phe Val Ile Val Ser Trp Arg Asn Leu Pro Leu Val Ser Ile
                165                 170                 175
```

-continued

```
Asn Asp Pro Ile Leu Met Ile Lys Lys Pro Ala Gly Leu Thr Ala Ala
            180                 185                 190

Thr Gly Met Asp Ala Leu Thr His Ala Ile Glu Ser Tyr Val Ser Lys
        195                 200                 205

Asp Ala Asn Pro Val Thr Asp Ala Leu Ala Ile Gln Ala Ile Lys Leu
    210                 215                 220

Ile Ala Asn Asn Leu Arg Gln Ala Val Ala Leu Gly Glu Asn Leu Glu
225                 230                 235                 240

Ala Arg Glu Asn Met Ala Tyr Ala Ser Leu Leu Ala Gly Met Ala Phe
                245                 250                 255

Asn Asn Ala Asn Leu Gly Tyr Val His Ala Met Ala His Gln Leu Gly
            260                 265                 270

Gly Leu Tyr Asp Met Ala His Gly Val Ala Asn Ala Met Leu Leu Pro
        275                 280                 285

His Val Glu Arg Tyr Asn Leu Ile Ser Asn Pro Lys Lys Phe Ala Asp
    290                 295                 300

Ile Ala Glu Phe Met Gly Glu Asn Ile Glu Gly Leu Ser Val Met Glu
305                 310                 315                 320

Ala Ala Glu Lys Ala Ile Asp Ala Met Phe Arg Leu Ser Lys Asp Val
                325                 330                 335

Gly Ile Pro Ala Ser Leu Lys Glu Met Gly Val Asn Glu Gly Asp Phe
            340                 345                 350

Glu Tyr Met Ala Lys Met Ala Leu Lys Asp Gly Asn Ala Phe Ser Asn
        355                 360                 365

Pro Arg Lys Gly Asn Glu Lys Asp Ile Val Lys Ile Phe Arg Glu Ala
    370                 375                 380

Phe
385
```

MUTANT 1,3-PROPANEDIOL DEHYDROGENASE

This is a divisional of application Ser. No. 09/500,778, filed May 14, 2000, and claims the benefit of provisional application No. 60/134,868, filed May 19, 1999.

FIELD OF THE INVENTION

The present invention relates to mutant 1,3-propanediol dehydrogenase having an altered Km for 1,3-propanediol. The present invention provides the nucleic acid and amino acid sequence of the mutant form of 1,3-propanediol dehydrogenase. The present invention also provides expression vectors and host cells comprising mutant 1,3-propanediol dehydrogenase.

BACKGROUND OF THE INVENTION 1,3-Propanediol is a monomer having potential utility in the production of polyester fibers and the manufacture of polyurethanes and cyclic compounds. The production of 1,3-propanediol has been disclosed in U.S. Pat. No. 5,686,276 issued Nov. 11, 1997 and WO 98/21341. One representative pathway for the production of 1,3-propanediol from glucose can be accomplished by the following series of steps. Glucose is converted in a series of steps by enzymes of the glycolytic pathway to dihydroxyacetone phosphate (DHAP) and 3-phosphoglyceraldehyde (3-PG). Glycerol is then formed by either hydrolysis of DHAP to dihydroxyacetone (DHA) followed by reduction, or reduction of DHAP to glycerol 3-phosphate (G3P) followed by hydrolysis. The hydrolysis step can be catalyzed by any number of cellular phosphatases which are known to be specific or non-specific with respect to their substrates or the activity can be introduced into the host by recombination. The reduction step can be catalyzed by a $NAD^+$ (or $NADP^+$) linked host enzyme or the activity can be introduced into the host by recombination. It is notable that the dha regulon contains a glycerol dehydrogenase (E.C. 1.1.1.6) which catalyzes the reversible reaction of Equation 3.

$$\text{Glycerol} \rightarrow \text{3-HP} + H_2O \qquad \text{(Equation 1)}$$

$$\text{3-HP} + NADH + H^+ \rightarrow \text{1,3-Propanediol} + NAD^+ \qquad \text{(Equation 2)}$$

$$\text{Glycerol} + NAD^+ \rightarrow DHA + NADH + H^+ \qquad \text{(Equation 3)}$$

Glycerol is converted to 1,3-propanediol via the intermediate 3-hydroxypropionaldehye (3-HP) as has been described in detail above. The intermediate 3-HP is produced from glycerol (Equation 1) by a dehydratase enzyme which can be encoded by the host or can introduced into the host by recombination. This dehydratase can be glycerol dehydratase (E.C. 4.2.1.30), diol dehydratase (E.C. 4.2.1.28), or any other enzyme able to catalyze this transformation. Glycerol dehydratase is encoded by the dha regulon. 1,3-Propanediol is produced from 3-HP (Equation 2) by a $NAD^+$-(or $NADP^+$) linked host enzyme or the activity can introduced into the host by recombination. This final reaction in the production of 1,3-propanediol can be catalyzed by 1,3-propanediol dehydrogenase (E.C. 1.1.1.202) or other alcohol dehydrogenases.

In *Klebsiella pneumoniae* and *Citrobacter freundii*, the genes encoding the functionally linked activities of glycerol dehydratase (dhaB), 1,3-propanediol oxidoreductase (dhaT), glycerol dehydrogenase (dhaD), and dihydroxyacetone kinase (dhaK) are encompassed by the dha regulon. The dha regulons from Citrobacter and Klebsiella have been expressed in *Escherichia coli* and have been shown to convert glycerol to 1,3-propanediol.

Nucleic acid and amino acid sequences for a 1,3-propanediol dehydrogenase that have been disclosed in the art, including *Klebsiella pneumoniae* GenBank accession #U30903 (Williard, 1994, "Investigation of the *Klebsiella pneumoniae* 1,3-propanediol pathway: Characterization and expression of glycerol dehydratase and 1,3-propanediol oxidoreductase" Thesis Chemical Engineering, University of Wisconsin-Madison); *Citrobacter freundii* GenBank accession #U09771 (Daniel, R. et al., 1995, Purification of 1,3-propanediol dehydrogenase from Citrobacter freundii: cloning, sequencing, and overexpression of the corresponding gene in *Escherichia coli. J. Bacteriol.* 177:2151–2156); and *Clostridium pasteurianum* GenBank accession #AF006034 (Luers, F. et al., 1997, Glycerol conversion to 1,3-propanediol by *Clostridium pasteurianum*: cloning and expression of the gene encoding 1,3-propanediol dehydrogenase. *FEMS Microbiol. Lett.* 154:337–345).

SUMMARY OF THE INVENTION

The present invention relates to the discovery of a mutant form of 1,3-propanediol dehydrogenase (PDD) isolated from a derivative of *E. blattae* capable of growth in the presence of at least 105 g/l 1,3-propanediol, levels normally toxic to wild-type *E. blattae*. The present invention is therefore based in part upon the discovery that the mutant form of PDD is associated with *E. blattae's* resistance to normally toxic levels of 1,3-propanediol. The present invention is also based in part upon the finding that this mutant PDD has an altered Km for 1,3-propanediol and NAD.

Accordingly, the present invention provides a mutant PDD having a Km for 1,3-propanediol that is increased over the wild-type PDD Km for 1,3-propanediol. In one embodiment, the Km of the mutant PDD is about 3 times the Km of wild-type PDD for 1,3-propanediol. In another embodiment, the mutant PDD has a Km of about 80 mM for 1,3-propanediol. In a further embodiment, the mutant PDD is obtainable from *E. blattae* ATCC accession number PTA-92.

In yet another embodiment of the present invention, the mutant PDD comprises a mutation corresponding to residue His 105 to Leu in *E. blatte* PDD as shown in FIG. 3. In an additional embodiment, the mutant PDD comprises the amino acid shown in SEQ ID NO:2 and is encoded by nucleic acid having the sequence as shown in SEQ ID NO:1.

The present invention also provides expression vectors and host cells comprising the isolated nucleic acid having the sequence as shown in SEQ ID NO:1. In one embodiment, the host cell includes Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces and Pseudomonas.

In an additional aspect, the present invention relates to methods for producing 1,3-propanediol comprising the use of a microorganism comprising mutant PDD.

BRIEF DESCRIPTION OF THE DRAWINGS

FIG. 1 provides the nucleic acid sequence (SEQ ID NO: 1) for the mutant 1,3-propanediol dehydrogenase (PDD) and the nucleic acid sequence for wild-type *E. blattae* designated Eb_429T (ATCC accession number 33429) (SEQ ID NO: 5).

FIG. 2 provides the amino acid sequence (SEQ ID NO: 2) for the mutant 1,3-propanediol dehydrogenase (PDD) and the amino acid sequence for wild-type Eb_429T (SEQ ID NO: 6).

FIG. 3 provides an amino acid sequence alignment of PDDs from various microorganisms. Eb—GEBT represents the PDD from the ATCC deposited *E. blattae* mutant PDD (SEQ ID NO: 2); Eb_429T (SEQ ID NO: 6) and Eb_907T (SEQ ID NO: 7) represent PDDs from wild type *E. blattae* (Eb_429T is ATCC accession number 33429); Kpn (SEQ ID NO: 8) represents the PDD from *Klebsiella pneumoniae* (GenBank accession #U30903); Cfu (SEQ ID NO: 9) represents the PDD from *Citrobacter freundii* (GenBank accession number U09771) and Cpast (SEQ ID NO: 10) represents the PDD from *Clostridium pasteurianum* (GenBank accession number AF006034).

DESCRIPTION OF THE MICROORGANISM DEPOSITS MADE UNDER THE BUDAPEST TREATY

Applicants have made the following biological deposits under the terms of the Budapest Treaty on the International Recognition of the Deposit of Micro-organisms for the Purposes of Patent Procedure:

| Depositor Identification Reference | International Depository Designation | Date of Deposit |
| --- | --- | --- |
| *Escherichia blattae* 33429 derivative | PTA-92 | May 19, 1999 |

Detailed Description

Definitions

The terms "1,3-propanediol dehydrogenase" or "PDD" (also known in the art as "oxidoreductase") refer to the polypeptide(s) responsible for an enzyme activity that is capable of catalyzing the reduction of 3-hydroxypropionaldehyde to 1,3-propanediol. 1,3-Propanediol dehydrogenase includes, for example, the polypeptide encoded by the dhaT gene. The present invention encompasses 1,3-propanediol dehydrogenase from any source including, but not limited to *E. blatte, K. pneumoniae, C. freundii, C. pasteurianum.*

As used herein, the term "mutant" or "mutation" refers to any genetic change that occurs in the nucleic acid of a microorganism and may or may not reflect a phenotypic change within the microorganism. A mutation may comprise a single base pair change, deletion or insertion; a mutation may comprise a change, deletion or insertion in a large number of base pairs; a mutation may also comprise a change in a large region of DNA, such as through duplication or inversion. The amino acid sequence of a mutant 1,3-propanediol dehydrogenase can be derived from a precursor 1,3-propanediol dehydrogenase by the substitution, deletion or insertion of one or more amino acids of the naturally occurring 1,3-propanediol dehydrogenase. Methods for modifying genes (e.g., through site-directed oligonucleotide mutagenesis) have been described in the art.

The phrase "corresponding to" as used herein refers to the amino acid relatedness among 1,3-propanediol dehydrogenases as exemplified by FIG. 3. Specific residues discussed herein refer to an amino acid residue number which references the number assigned to the *E. blatte* GEB PDD shown in FIG. 3. The mutation of His to Leu is shown at residue 105 in FIG. 3. FIG. 3 illustrates that 1,3-propanediol dehydrogenases from a variety of microbial sources can be aligned using the algorithm CLUSTALW. The invention is not limited to the mutation of the *E. blattae* PDD shown in FIGS. 1 and 2, or the *E. blattae* deposited with the ATCC and having accession number PTA-92 but encompasses all PDDs containing amino acid residues at positions which are equivalent to the particular identified residue in *E. blattae*. A residue is equivalent if it is either homologous (i.e., corresponds in position for either the primary or tertiary structure) or analogous to a specific residue or portion of that residue in *E. blattae* PDD (i.e., having the same or similar functional capacity to combine, react, or interact chemically or structurally).

In order to establish homology to primary structure, the amino acid sequence of a PDD is directly compared to the *E. blattae* PDD primary sequence (shown in FIG. 2) and particularly to a set of residues known to be invariant to all PDDs for which sequences are known (see, e.g., FIG. 3). The present invention encompasses the equivalent residue change in all sources of 1,3-propanediol dehydrogenase as long as the mutant form is able to alter the Km of the activity for 1,3-propanediol. In a preferred embodiment, the Km of the mutant form is increased for 1,3-propanediol. The nucleic acid sequence of SEQ ID NO:1 was obtained via PCR techniques. Such techniques are often characterized by inadvertent PCR generated sequence error. Therefore, the present invention also encompasses the 1,3-propanediol dehydrogenase of *E. blattae* having ATCC accession number PTA-92 and corresponding mutations in other microbial sources of the 1,3-propanediol dehydrogenases.

The term "Km" refers to affinity of the enzyme for the substrate. A high Km reflects a low affinity; a low Km reflects a high affinity.

The terms "carbon substrate" and "carbon source" refer to a carbon source capable of being metabolized by host organisms of the present invention and particularly carbon sources selected from the group consisting of monosaccharides, oligosaccharides, polysaccharides, and one-carbon substrates or mixtures thereof.

The terms "host cell" or "host organism" refer to a microorganism capable of receiving foreign or heterologous genes and of expressing those genes to produce an active gene product.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. The terms "native" and "wild-type" refer to a gene as found in nature with its own regulatory sequences. As used herein "amino acid" refers to peptide or protein sequences or portions thereof.

The term "expression" refers to the transcription and translation to gene product from a gene coding for the sequence of the gene product.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The terms "isolated" or "purified" as used herein refer to a nucleic acid or amino acid that is removed from at least one component with which it is naturally associated.

DETAILED DESCRIPTION OF THE INVENTION

The present invention relates to mutant 1,3-propanediol dehydrogenase (PDD) characterized by having an increased Km for 1,3 propanediol.

PDD Sequences

Polynucleotide sequence as shown in SEQ ID NO:1 encodes the 1,3-propanediol dehydrogenase (SEQ ID NO:2) having the mutation of His to Leu at residue 105 as shown in FIG. 3. As will be understood by the skilled artisan, due to the degeneracy of the genetic code, a variety of polynucleotides can encode SEQ ID NO:2. The present invention encompasses all such polynucleotides. The present invention encompasses nucleic acid encoding PDD comprising a mutation corresponding to *E. blatte* residue His 105 to Leu as shown in FIG. 3. The nucleic acid and amino acid sequence for PDD from *K. pneumoniae* is given in GenBank accession number U30903; PDD from *C. freundii* is given in GenBank accession number U09771; for PDD from *C. pasteurianum* is given in GenBank accession number AF00034. The present invention also encompasses mutant PDD obtainable from *E. blattae* having ATCC accession number PTA-92.

Methods of obtaining desired genes from a microbial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of DNA suitable for transformation using appropriate vectors.

Alternatively, methods of using cosmid vectors for the transformation of suitable bacterial hosts are well described in Sambrook et al., *Molecular Cloning: A Laboratory Manual*, Second Edition (1989) Cold Spring Harbor Laboratory Press, Cold Spring Harbon, N.Y. (1989).

Methods of making mutations in PDD genes are known to the skilled artisan and include for example site-directed mutagenesis, procedures described in U.S. Pat. No. 4,760, 025 issued Jul. 26, 1988.

Vectors and Expression Cassettes

The present invention provides a variety of vectors and transformation and expression cassettes suitable for the cloning, transformation and expression of mutant PDD as well as other proteins associated with 1,3-propanediol production into a suitable host cell. Suitable vectors will be those which are compatible with the bacterium employed. Suitable vectors can be derived, for example, from a bacteria, a virus (such as bacteriophage T7 or a M-13 derived phage), a cosmid, a yeast or a plant. Protocols for obtaining and using such vectors are known to those in the art. (Sambrook et al., Molecular Cloning: A Laboratory Manual—volumes 1,2,3 (Cold Spring Harbor Laboratory, Cold Spring Harbor, N.Y., (1989)).

Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell although it is to be understood that such control regions need not be derived from the genes native to the specific species chosen as a production host.

Initiation control regions or promoters, which are useful to drive expression of PDD in the desired host cell, are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $IP_L$, $IP_R$, T7, tac, and trc (useful for expression in *E. coli*).

Termination control regions may also be derived from various genes native to the preferred hosts. Optionally, a termination site may be unnecessary, however, it is most preferred if included.

For effective expression of the instant enzymes, DNA encoding the enzymes are linked operably through initiation codons to selected expression control regions such that expression results in the formation of the appropriate messenger RNA.

Transformation of Suitable Hosts and Expression of PDD

Once suitable cassettes are constructed they are used to transform appropriate host cells. Introduction of the cassette containing mutant 1,3-propanediol dehydrogenase, either separately or together with other proteins necessary for the production of 1,3-propanediol, into the host cell may be accomplished by known procedures such as by transformation (e.g., using calcium-permeabilized cells, electroporation) or by transfection using a recombinant phage virus. (Sambrook et al., supra.).

Host Cells

Suitable host cells for the recombinant production of 1,3-propanediol may be either prokaryotic or eukaryotic and will be limited only by the host cell ability to express active enzymes. Preferred hosts will be those typically useful for production of glycerol or 1,3-propanediol such as Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces and Pseudomonas. Most preferred in the present invention are *E. coli*, Klebsiella species and Saccharomyces species.

Media and Carbon Substrates:

Fermentation media in the present invention must contain suitable carbon substrates. Suitable substrates may include but are not limited to monosaccharides such as glucose and fructose, oligosaccharides such as lactose or sucrose, polysaccharides such as starch or cellulose, or mixtures thereof, and unpurified mixtures from renewable feedstocks such as cheese whey permeate, cornsteep liquor, sugar beet molasses, and barley malt. Additionally, the carbon substrate may also be one-carbon substrates such as carbon dioxide, or methanol for which metabolic conversion into key biochemical intermediates has been demonstrated.

Preferred carbon substrates are monosaccharides, oligosaccharides, polysaccharides, and one-carbon substrates. More preferred are sugars such as glucose, fructose, sucrose and single carbon substrates such as methanol and carbon dioxide. Most preferred is glucose.

In addition to an appropriate carbon source, fermentation media must contain suitable minerals, salts, cofactors, buffers and other components, known to those skilled in the art, suitable for the growth of the cultures and promotion of the enzymatic pathway necessary for glycerol production. Particular attention is given to Co(II) salts and/or vitamin $B_{12}$ or precursors thereof.

Culture Conditions:

Typically, cells are grown at 30° C. in appropriate media. Preferred growth media in the present invention are common commercially prepared media such as Luria Bertani (LB) broth, Sabouraud Dextrose (SD) broth or Yeast Malt Extract (YM) broth. Other defined or synthetic growth media may also be used and the appropriate medium for growth of the particular microorganism will be known by someone skilled in the art of microbiology or fermentation science. The use of agents known to modulate catabolite repression directly or indirectly, e.g., cyclic adenosine 2':3'-monophosphate or cyclic adenosine 2':5'-monophosphate, may also be incorporated into the reaction media. Similarly, the use of agents known to modulate enzymatic activities (e.g., sulphites, bisulphites and alkalis) that lead to enhancement of glycerol production may be used in conjunction with or as an alternative to genetic manipulations.

Suitable pH ranges for the fermentation are between pH 5.0 to pH 9.0, where pH 6.0 to pH 8.0 is preferred as range for the initial condition.

Reactions may be performed under aerobic or anaerobic conditions where anaerobic or microaerobic conditions are preferred.

The manner and method of carrying out the present invention may be more fully understood by those of skill in the art by reference to the following examples, which examples are not intended in any manner to limit the scope of the present invention or of the claims directed thereto.

EXAMPLES

Example 1

Describes the Kinetic Changes Associated with the Mutant PDD Shown in SEQ ID NO:2.

Materials and Methods

Strains—Wild type ATCC 33429, *E. blattae* comprising the mutant PDD ATCC accession number PTA-92.

Growth—Cells were grown in a complex medium at 30C 500 ml in a 2800 ml fernbach with shaking at 225 rpm for 20 hr. The medium consists of KH2PO4, 5.4 g/L; (NH4) 2SO4, 1.2 g/L; MgSO47H2O, 0.4 g/L; yeast extract, 2.0 g/L; tryptone, 2.0 g/L; and glycerol, 9.2 g/L in tap water. The pH was adjusted to 7.1 with KOH before autoclaving (Honda, et al., 1980, *J. Bacteriol*, 143:1458–1465).

Extract prep—Cells were harvested by centrifugation with care to avoid anaerobic conditions. Pellets were resuspended in 100 mM Tricine pH 8.2 containing 50 mM KCl and 1 mM DTT. Cells were disrupted by passage through a French pressure cell. Crude extracts were clarified by centrifugation at 20 K×g for 20 min followed by 100 K×g for 1 hr to yield the high speed supernatant (HSS) fraction.

Assays—the assay for PDD was performed as described by Johnson, E. A. et al., 1987, *J. Bacteriol.* 169:2050–2054.

Partial purification of PDD—HSS was separated on a 16×100 Poros 20HQ column. The buffers were A, 60 mM HEPES, pH 7.4 containing 100 uM MnCl and B, A buffer containing 500 mM KCl. The column was loaded and developed at 10 ml/min. The gradient was 10 CV wash. A linear gradient to 70% B in 10 CV, and 1 CV to 100% B. The activity was detected in the very early fractions of the gradient. Pooled column fractions of the 33429 strain were used as collected for assays after the addition of additional DTT to 1 mM. The active fractions from the *E. blattae* 33429 derivative strain assigned designation PTA-92 were pooled and concentrated on a PM30 membrane and used as concentrated after the addition of additional 1 mM DTT.

| Strain | GD (U/mg) | PDD (U/mg) | Ratio GD/PDD |
|---|---|---|---|
| 33429 | 0.64 | 0.22 | 2.9 |
| PTA-92 | 0.79 | 0.08 | 9.9 |

| Strain | Km (mM Propanediol) | Km (UM, NAD) |
|---|---|---|
| 33429 | 28 | 57 |

Example 2

Cloning and Sequencing the 1,3-Propanediol Dehydrogenase Genes (dhaT) from *E. blattae.*

The dhaT genes were amplified by PCR from genomic DNA from *E. blattae* as template DNA using synthetic primers (Primer 1, SEQ ID NO: 3 and primer 2, SEQ ID NO: 4) based on the *K. pneumoniae* dhaT sequence and incorporating an Xbal site at the 5' end and a BamHl site at the 3' end. The product was subcloned into pCR-Blunt II-TOPO (Invitrogen). The cloning dhaT were then sequenced by standard techniques.

The results of the DNA sequencing are given in SEQ ID NO: 1 and SEQ ID NO: 2.

Primer 1

5'TCTGATACGGGATCCTCAGAAMTGCCTGGCGGAAAAT3' SEQ ID NO: 3

Primer 2

5'GCGCCGTCTAGAATTATGAGCTATCGTATGTTTGATTATCTG3' SEQ ID NO: 4

As will be readily understood by the skilled artisan, nucleic acid sequences generated via PCR methods may comprise inadvertent errors. The present invention also encompasses nucleic acid sequences encoding PDD obtainable from *E. blattae* having ATCC accession number PTA-92.

All references cited herein, including patents, patent applications, sequences and publications are hereby incorporated in their entirety by reference.

What is claimed is:

1. An isolated nucleic acid encoding mutant 1,3-propanediol dehydrogenase having the sequence as shown in SEQ ID NO:2.

2. The isolated nucleic acid of claim 1 having the sequence as shown in SEQ ID NO:1.

3. An expression vector comprising the isolated nucleic acid of claim 1.

4. A host cell comprising the expression vector of claim 3.

5. The host cell of claim 4 that is Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces or Pseudomonas.

6. A method for making 1,3-propanediol in a bacterial host cell comprising the steps of a) obtaining a bacterial host cell comprising a mutant 1,3-propanediol dehydrogenase (PDD) which is obtainable from a bacterial cell wherein said mutant PDD comprises a mutation corresponding to residue Hisl05 to Leu in *E. blattae* shown in SEQ ID NO: 5 or SEQ ID NO 6 wherein said mutant PDD has an increased Km for 1,3-propanediol over the corresponding wild-type and said bacterial host cell comprising at least one gene capable of expressing a dehydratase, and b) contacting the bacterial host cell with a carbon substrate.

7. An isolated microorganism having ATCC accession number PTA-92.

8. A method for the production of 1,3-propanediol dehydrogenase by a microbial host cell comprising:

a) transforming the host cell with the polynucleotide according to claim 7, and b) culturing the transformed host cell under suitable conditions to allow expression of the 1,3-propanediol dehydrogenase.

9. The method according to claim 8, wherein the polynucleotide sequence is the sequence shown in SEQ ID NO: 1.

10. The method according to claim 8, wherein the microbial host cell is selected from the group consisting of Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces and Pseudomonas.

11. The method according to claim 10, wherein the microbial host cell is selected from a Klebsiella, Saccharomyces or Escherichia host cell.

12. A method for the production of 1,3-propanediol by a microbial host cell comprising:

a) transforming a host cell with a polynucleotide encoding a mutant 1,3-propanediol dehydrogenase wherein the mutant 1,3-propanediol dehydrogenase comprises a mutation from His to Leu in a position corresponding to amino acid residue position 105 in SEQ ID NO: 2, and wherein the mutant dehydrogenase has a Km for 1,3-propanediol which is increased over the Km of the corresponding wild-type 1,3-propanediol dehydrogenase for 1,3-propanediol, wherein the host cell comprises at least one gene capable of expressing a dehydratase enzyme, and b) culturing said transformed host cell under suitable conditions to allow expression of said mutant 1,3-propanediol dehydrogenase and production of 1,3-propanediol.

13. The method according to claim 12, wherein the mutant 1,3-propanediol dehydrogenase has a Km for 1,3-propanediol which is about three times the Km of the corresponding wild-type 1,3-propanediol dehydrogenase for 1,3-propanediol.

14. A method for the production of 1,3-propanediol dehydrogenase by a microbial host cell comprising:

a) transforming the host cell with a polynucleotide encoding a mutant 1,3-propanediol dehydrogenase wherein the mutant 1,3-propanediol dehydrogenase comprises a mutation in a position corresponding to amino acid residue position 105 in SEQ ID NO: 2, and wherein the mutant dehydrogenase has a Km for 1,3-propanediol which is about three times the Km of the corresponding wild-type 1,3-propanediol dehydrogenase for 1,3-propanediol, and b) culturing said transformed host cell under suitable conditions to allow expression of said mutant 1,3-propanediol dehydrogenase.

15. The method according to claim 14, wherein the microbial host cell is selected from a Klebsiella, Saccharomyces or Escherichia host cell.

16. The method according to claim 12, wherein the mutant 1,3-propanediol dehydrogenase is obtained from a bacteria selected from the group consisting of Klebsiella, Escherichia, Citrobacter and Clostridium.

17. The host cell of claim 12, wherein said host cell is selected from the group consisting of Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces and Pseudomonas.

18. The host cell of claim 17, wherein said host cell is selected from the group consisting of Klebsiella, Saccharomyces, Escherichia, and Bacillus.

19. The host cell of claim 4, wherein the host cell is selected from the group consisting of Klebsiella, Saccharomyces, Escherichia, and Bacillus.

20. The method according to claim 6, wherein the host cell is selected from the group consisting of Klebsiella, Saccharomyces, Escherichia, and Bacillus.

21. The method according to claim 16, wherein the mutant 1,3-propanediol dehydrogenase is obtained from a *Klebsiella pneumoniae*, an *Escherichia blattae*, a *Citrobacter freundii* or a *Clostridium pasteurianum*.

22. The method according to claim 12, wherein the DNA encoding the mutant 1,3-propanediol dehydrogenase is obtainable from *E. blattae* having ATCC accession number PTA-92.

* * * * *